US008883153B2

(12) United States Patent
Ghebrehiwet (10) Patent No.: US 8,883,153 B2
(45) Date of Patent: Nov. 11, 2014

(54) METHODS FOR PREVENTING AND TREATING ANGIOEDEMA

(75) Inventor: Berhane Ghebrehiwet, Port Jefferson, NY (US)

(73) Assignee: The Research for The State University of New York, Albany, NY (US)

( * ) Notice: Subject to any disclaimer, the term of this patent is extended or adjusted under 35 U.S.C. 154(b) by 0 days.

(21) Appl. No.: 13/260,664

(22) PCT Filed: Mar. 29, 2010

(86) PCT No.: PCT/US2010/029052
§ 371 (c)(1),
(2), (4) Date: Dec. 16, 2011

(87) PCT Pub. No.: WO2010/111702
PCT Pub. Date: Sep. 30, 2010

(65) Prior Publication Data
US 2012/0082676 A1    Apr. 5, 2012

Related U.S. Application Data

(60) Provisional application No. 61/164,197, filed on Mar. 27, 2009.

(51) Int. Cl.
*A61K 39/395* (2006.01)
*A61K 38/04* (2006.01)
*C07K 16/00* (2006.01)
*C07K 7/18* (2006.01)
*C07K 7/08* (2006.01)

(52) U.S. Cl.
CPC ............. *A61K 38/04* (2013.01); *C07K 16/00* (2013.01); *C07K 2317/76* (2013.01); *C07K 7/18* (2013.01); *C07K 7/08* (2013.01)
USPC .......... 424/139.1; 424/133.1; 424/141.1; 424/143.1; 424/145.1; 424/185.1; 514/1.1; 514/12.5; 514/13.5

(58) Field of Classification Search
None
See application file for complete search history.

(56) References Cited

U.S. PATENT DOCUMENTS

| 4,946,778 | A | 8/1990 | Ladner et al. |
| 5,541,286 | A * | 7/1996 | Kyle .............................. 530/314 |
| 6,994,852 | B1 | 2/2006 | Colman et al. |
| 8,178,104 | B2 * | 5/2012 | Ruoslahti et al. .......... 424/193.1 |
| 2006/0115471 | A1 | 6/2006 | Colman et al. |
| 2008/0014143 | A1 | 1/2008 | Ruoslahti et al. |

FOREIGN PATENT DOCUMENTS

| WO | 88/09344 A1 | 12/1988 |
| WO | 92/01047 A1 | 1/1992 |
| WO | 93/11236 A1 | 6/1993 |
| WO | WO 0027415 A2 * | 5/2000 |
| WO | 2005/061535 A1 | 7/2005 |
| WO | WO 2005061535 A1 * | 7/2005 |

OTHER PUBLICATIONS

Peerschke et al., Infect Immun. Aug. 2006; 74(8): 4418-4423.*
Joseph et al., Biol Chem. Jan. 2001;382(1):71-5.*
Ghebrehiwet et al., Immunol Rev. Apr. 2001;180:65-77.*
Cugno et al., Int Immunopharmacol. Mar. 2003;3(3):311-7.*
Grigoriadou S, and Longhurst HJ., Clin Exp Immunol. Mar. 2009;155(3):367-77. doi: 10.1111/j.1365-2249.2008.03845.x.*
Peerschke, E. I. B. et al, "The Contribution of gC1qR/p33 in Infection and Inflamation", Immunobiology (2007), vol. 212, pp. 333-342.
Zuckermann, R.N. et al., "Discovery of Nanomolar Ligands for 7-Transmembrane G-Protein-Coupled Receptors from a Diverse N-(Substituted)Glycine Peptoid Library", J. Med. Chem. (1994); vol. 37; pp. 2678-2685.
Agah, R. et al., "Angioedema: The Role of ACE Inhibitors and Factors Associated With Poor Clinical Outcome", Intensive Care Med. (1997); vol. 23; pp. 793-796.
Arnon, R. et al., "Complexes and Conjugates of CIS-Pt for Immunotargeted Chemotherapy", Adv. Exp. Med. Biol. (1991), vol. 303; pp. 79-90. In Immunobiology of Proteins and Peptides VI Human Immunodeficiency Virus, Antibody Immunocongjugates, Bacterial Vaccines, and Immunomodulators (edited by M. Zouhair Atassi).
Beltrani, V. "Angioedema: Some "New" Thoughts Regarding Idiopathic Angioedema", In Urticaria and angioedema (Greaves MW, and AP Kaplan editors) (2004) pp. 421-439.
Black, S. et al., "Minireview: C-reactive Protein", The Journal of Biological Chemistry (2004), vol. 279:47; pp. 48487-48490.
Boerner, P. et al., "Production of Antigen-Specific Human Monoclonal Antibodies From In Vitro-Primed Human Splenocytes", J. Immunology. (1991); vol. 147:1; pp. 86-95.
Bossi, F., et al., "Platelet-Activating Factor and Kinin-Dependent Vascular Leakage as a Novel Functional Activity of the Soluble Terminal Complement Complex", J. Immunol. (2004) vol. 173; pp. 6921-6927.
Bossi, F., et al., "Novel Pathogenic Mechanism and Therapeutic Approaches to Angioedema Associated with C1 Inhibitor Deficiency", J. Allergy Clin. Immunol. (2009); vol. 124:6; pp. 1303-1310.
Colman, R., et al., "Binding of High Molecular Weight Kininogen to Human Endothelial Cells is Mediated Via a Site Within Domains 2 and 3 of the Urokinase Receptor", J. Clin. Invest (1997); vol. 100:6; pp. 1481-1487.
Davis, C., "New treatment addressing the pathophysiology of hereditary angioedema", Clinical and Molecular Allergy (2008), vol. 6:2; 7 pages.
Fox, R., et al., "Arteriolar Flow Recruitment with Vitronectin Receptor Stimulation Linked to Remote Wall Shear Stress", Microvasc. Res. (2002) vol. 64; pp. 414-424.
Frame, M. et al., "Diminished Arteriolar Responses in Nitrate Tolerance Involve ROS and Angiotensin II", Am J of Physiol Heart Circulation Physiol (2002); vol. 282; pp. H2377-H2385.

(Continued)

*Primary Examiner* — Michael Szperka
(74) *Attorney, Agent, or Firm* — Kenyon & Kenyon LLP (57) ABSTRACT

One aspect of the present invention provides a method of treating or preventing angioedema in a patient in need thereof comprising administering to the patient a therapeutically effective amount of an agent that is capable of inhibiting the interaction of HK with gC1q-R. One aspect of the present invention provides a method of treating or preventing vascular permeability in a patient in need thereof comprising administering to the patient a therapeutically effective amount of an agent that is capable of inhibiting the interaction of HK with gC1q-R.

6 Claims, 4 Drawing Sheets

(56) References Cited

OTHER PUBLICATIONS

Frame, M. et al., "Remote Microvascular Preconditioning Alters Specific Vasoactive Responses", Microcirculation (2007); vol. 14; pp. 739-754.
Genbank accession No. NM_001102416.1 (GI:156231036); "*Homo sapiens* kininogen 1 (KNG1, transcript variant 1, mRNA" (2009).
Ghebrehiwet, B., et al., "Isolation cDNA Cloning, and Overexpression of a 33-kD Cell Surface Glycoprotein That Binds to the Globular "Heads" of C1q", J. Exp. Med. (1994); vol. 179; pp. 1809-1821.
Ghebrehiwet, B. et al., "Structure and Function of gC1q-R: a Multiligand Binding Cellular Protein", Immunobiol. (1998), vol. 199, pp. 225-238.
Ghebrehiwet, B., et al., "gC1q-R/p33: Structure-Function Predictions from the Crystal Structure", Immunobiol. (2002); vol. 205; pp. 421-432.
Ghebrehiwet, B., et al., "cC1q-R (calreticulin) and gC1q-R/p33: ubiquitously expressed multi-ligand binding cellular proteins involved in inflammation and infection", Molecular Immunology (2004); vol. 41; pp. 173-183.
Ghebrehiwet, B., et al., "Interaction of C1q with the Endothelium: Relevance to Inflammation", (2006) Chapter 109, pp. 741-743.
Ghebrehiwet, B. et al., "The exosporium of *B. cereus* contains a binding site for gC1qR/p33: implication in spore attachment and/or entry"; Adv. Exp. Med. Biol. (2007); vol. 598; pp. 181-197.
Greenfield, R., et al., "Evaluation in Vitro of Adriamycin Immunoconjugates Synthesized Using an Acid Sensitive Hydrazone Linker", Cancer Research (1990); vol. 50; pp. 6600-6607.
Hasan, A. et al., "Identification of Cytokeratin 1 as a Binding Protein and Presentation Receptor for Kininogens on Endothelial Cells", Proc. Natl. Acad. Sci. USA (1998) vol. 95; pp. 3615-3620.
Hasan, A. et al. "Mapping the cell binding site on high molecular weight kininogen domain 5", J. Biol. Chem. (1995); vol. 270; pp. 19256-19261.
Hawkins, R. et al., "Selection of Phage Antibodies by Binding Affinity Mimicking Affinity Maturation", J. Mol. Biol. (1992); vol. 226; pp. 889-896.
Herwald, H. et al., "Identification of an Endothelial Cell Binding Site on Kininogen Domain D3", J. Biol. Chem. (1995); vol. 270:24; pp. 14634-14642.
Herwald, H. et al., "Isolation and Characterization of the Kininogen-Binding Protein p33 from Endothelial Cells", J. Biol. Chem. (1996), vol. 271:22, pp. 13040-13047.
Hoogenboom, H. et al., "By-Passing Immunisation: Human Antibodies from Synthetic Repertoires of Germline VH Gene Segments Rearranged In Vitro", J. Mol. Biol. (1991); vol. 227; pp. 381.
Houghten, R.A. "General Method for the Rapid Solid-Phase Synthesis of Large Numbers of Peptides: Specificity of Antigen-Antibody Interaction at the Level of Individual Amino Acids", Proc. Natl. Acad. Sci. USA (1985); vol. 82; pp. 5131-5135.
Jiang, J. et al., "Crystal Structure of Human p32, a Doughnut-Shaped Acidic Mitochondrial Matrix Protein", PNAS USA (1999), vol. 96; pp. 3572-3577.
Joseph, K. et al., "Cytokeratin-1 and gC1q-R Mediate High Molecular Weight Kininogen Binding to Endothelial Cells", Clin. Immunol. (1999); vol. 92:3; pp. 246-255.
Joseph, K, et al., "Interaction of High Molecular Weight Kininogen Binding Proteins on Endothelial Cells", J. Thromb. Haemost. (2004); vol. 91; pp. 61-70.
Kaplan, A.P. "Mechanisms of Bradykinin Generation", in Urticaria and Angioedema (Greaves MW and AP Kaplan editors , Marcel Decker Inc. New York) (2004); pp. 51-72.
Kiseleva, N. et al., "Use of Antobodies to DNA Modified With Trans-Diaminedichloroplatinum for Identifying Specific DNA Sequences" Mol. Biol. (USSR) (1991) vol. 25:2, pp. 422-427.
Laakkonen, P. et al., "Antitumor activity of a homing peptide that targets tumor lymphatics and tumor cells" PNAS (2004); vol. 101:25; pp. 9381-9386.
Li, J. et al., "Human Antibodies for Immunotherapy Development Generated Via a Human B Cell Hybridoma Technology", Proc. Natl. Acad. Sci. USA (2006), vol. 103:10; pp. 3557-3562.
Low, N.M. et al., "Mimicking Somatic Hypermutation: Affinity Maturation of Antibodies Displayed on Bacteriophage Using a Bacterial Mutator Strain", J. Mol. Biol. (1996) vol. 260; pp. 359-368.
Mahdi, F. et al., "Expression and colocalization of Cytokeratin 1 and Urokinase Plasminogen Activator Receptor on Endothelial Cells", Blood (2001), vol. 97; pp. 2342-2350.
Mahdi, F. et al., "Factor XII Interacts with Multiprotein Assembly of Urokinase Plasminogen Activator Receptor, gC1q-R and Cytokeratin 1 on Endothelial Cell Membranes", Blood (2002) vol. 99:10; pp. 3585-3596.
Marks, J. et al., "By-Passing Immunization: Human Antibodies from V-gene Libraries Displayed on Phage", J. Mol. Bio. (1991), vol. 222; pp. 581-597.
Nguyen, T. et al., "*Staphylococcus aureus* Protein A Recognizes Platelet gC1qR/p33: a Novel Mechanism for Staphylococcal Interactions with Platelets", Infection and Immunity, (2000); vol. 68:4; pp. 2061-2068.
Peerschke, E. et al., "Expression of gC1q-R/p33 and its major ligands in human atherosclerotic lesions", Molecular Immunology (2004), vol. 41; pp. 759-766.
Peerschke, E. et al., "gC1qR/p33 Blockade Reduces *Staphylococcus aureus* Colonization of Target Tissues in an Animal Model of Infective Endocarditis", Infection and Immunity (2006), vol. 74:8; pp. 4418-4423.
Regoli, D.et al., "Pharmacology of Bradykinin and Related Kinins" Pharmacol. Rev. (1980) vol. 32:1; pp. 1-46.
Rivers, R. et al., "Technique for Using Video Microscopy and Indicator Dilution for Repeated Measurements of Cardiac Output in Small Animals", Anesthesiology (2001); vol. 94; pp. 489-495.
Rubinstein, D.B. et al., "Receptor for the Globular Heads of C1q (gC1q-R, p33, Hyaluronan-Binding Protein) is Preferentially Expressed by Adenocarcinoma Cells", Int. J. Cancer (2004); vol. 110; pp. 741-750.
Sabbele, N. et al., "The Effect of Cyclophosphamide on B Cells and "Background" Immunogolobulin-Secreting Cells in Mice" Immunopharmacology (1988) vol. 15: pp. 21-30.
Sabroe, A. et al., "What is Urticaria? Anatomical, Physiological and Histological Considerations and Classification" , in Urticaria and Angioedema (Greaves MW and AP Kaplan editors) (2004); pp. 1-18.
Traggiai, E. et al., "An Efficient Method to Make Human Monoclonal Antibodies from Memory B Cells: Potent Neutralization of SARS Coronavirus", Nat. Med. (2004); vol. 10:8; pp. 871-875.
Waggoner, S.N. et al., "gC1q Receptor Ligation Selectively Down-Regulates Human IL-12 Production through Activation of the Phosphoinositide 3-Kinase Pathway", The Journal of Immunology (2005); vol. 175; pp. 4706-4714.
Yang, H. et al., "Haematology: Second Kininase in man Blood Plasma" Nature (1967); vol. 215; pp. 1402-1403.
Yang, W. et al., "CDR Walking Mutagenesis for the Affinity Maturation of a Potent Human Anti-HIV-1 Antibody into the Picomolar Range", J. Mol. Biol., (1995); vol. 254; pp. 392-403.

* cited by examiner

SEQUENCE LISTING

```
<160> NUMBER OF SEQ ID NOS: 16

<210> SEQ ID NO 1
<211> LENGTH: 18
<212> TYPE: PRT
<213> ORGANISM: Homo sapiens

<400> SEQUENCE: 1

Thr Asp Gly Asp Lys Ala Phe Val Asp Phe Leu Ser Asp Glu Ile Lys
1               5                   10                  15

Glu Glu

<210> SEQ ID NO 2
<211> LENGTH: 19
<212> TYPE: PRT
<213> ORGANISM: Homo sapiens

<400> SEQUENCE: 2

Asp Gly Glu Glu Glu Pro Ser Gln Gly Gln Lys Val Glu Glu Gln Glu
1               5                   10                  15

Pro Glu Leu

<210> SEQ ID NO 3
<211> LENGTH: 5
<212> TYPE: PRT
<213> ORGANISM: Homo sapiens

<400> SEQUENCE: 3

Asp Gly Glu Glu Glu
1               5
```

```
<210> SEQ ID NO 4
<211> LENGTH: 8
<212> TYPE: PRT
<213> ORGANISM: Homo sapiens

<400> SEQUENCE: 4

Lys Asn Asp Gly Lys Lys Glu Leu
1               5

<210> SEQ ID NO 5
<211> LENGTH: 13
<212> TYPE: PRT
<213> ORGANISM: Homo sapiens

<400> SEQUENCE: 5

Glu Asp Glu Val Gly Gln Glu Asp Glu Ala Glu Ser Asp
1               5                   10

<210> SEQ ID NO 6
<211> LENGTH: 7
<212> TYPE: PRT
<213> ORGANISM: Homo sapiens

<400> SEQUENCE: 6

Glu Asp Glu Ala Glu Ser Asp
1               5

<210> SEQ ID NO 7
<211> LENGTH: 3
<212> TYPE: PRT
<213> ORGANISM: Homo sapiens

<400> SEQUENCE: 7

Glu Asp Glu
1

<210> SEQ ID NO 8
<211> LENGTH: 15
<212> TYPE: PRT
<213> ORGANISM: Homo sapiens

<400> SEQUENCE: 8

Phe Ser Ile Arg Glu Val Ser Phe Gln Ser Thr Gly Glu Ser Glu
1               5                   10                  15

<210> SEQ ID NO 9
<211> LENGTH: 4
<212> TYPE: PRT
<213> ORGANISM: Homo sapiens

<400> SEQUENCE: 9

Gly Glu Ser Glu
1

<210> SEQ ID NO 10
<211> LENGTH: 12
<212> TYPE: PRT
<213> ORGANISM: Homo sapiens

<400> SEQUENCE: 10

Gln Ser Thr Gly Glu Ser Glu Trp Lys Asp Thr Asn
1               5                   10

<210> SEQ ID NO 11
<211> LENGTH: 20
```

```
<212> TYPE: PRT
<213> ORGANISM: Homo sapiens

<400> SEQUENCE: 11

His Lys His Gly His Gly His Gly Lys His Lys Asn Lys Gly Lys Lys
1               5                   10                  15

Asn Gly Lys His
            20

<210> SEQ ID NO 12
<211> LENGTH: 12
<212> TYPE: PRT
<213> ORGANISM: Homo sapiens

<400> SEQUENCE: 12

Lys His Lys Asn Lys Gly Lys Lys Asn Gly Lys His
1               5                   10

<210> SEQ ID NO 13
<211> LENGTH: 10
<212> TYPE: PRT
<213> ORGANISM: Homo sapiens

<400> SEQUENCE: 13

His Lys His Gly His Gly His Gly Lys His
1               5                   10

<210> SEQ ID NO 14
<211> LENGTH: 10
<212> TYPE: PRT
<213> ORGANISM: Homo sapiens

<400> SEQUENCE: 14

Gly His Gly Lys His Lys Asn Lys Gly Lys
1               5                   10

<210> SEQ ID NO 15
<211> LENGTH: 10
<212> TYPE: PRT
<213> ORGANISM: Homo sapiens

<400> SEQUENCE: 15

Lys Asn Lys Gly Lys Lys Asn Gly Lys His
1               5                   10

<210> SEQ ID NO 16
<211> LENGTH: 5
<212> TYPE: PRT
<213> ORGANISM: Homo sapiens

<400> SEQUENCE: 16

Lys His Lys Asn Lys
1               5
```

METHODS FOR PREVENTING AND TREATING ANGIOEDEMA

CROSS-REFERENCE TO RELATED APPLICATIONS

This application claims priority to U.S. Application No. 61/164,197, filed Mar. 27, 2009, which is incorporated herein by reference in its entirety.

STATEMENT OF GOVERNMENT INTEREST

The invention was made with United States Government support under grant number AI060866 awarded by the National Institutes of Health. The Government has certain rights in the invention.

FIELD OF THE INVENTION

The invention relates to methods for treating and/or preventing bradykinin and/or complement mediated vascular permeability and angioedema.

BACKGROUND OF THE INVENTION

Angioedema is a clinical symptom reported to affect at least 20% of the population. It is readily recognized as a usually asymmetrical, non-erythematous, non-pruritic, non-pitting, localized, transient, episodic swelling of a soft body area involving lax skin, oropharyngolaryngeal tissue and/or gastrointestinal wall (Beltrani V. S. 2004: Angioedema: some new thoughts regarding idiopathic angioedema. In Urticaria and angioedema (Greaves, M. W., and A. P. Kaplan editors) pp. 421-439). The presence or absence of chronic recurrence of urticaria is a feature, which distinguishes the different forms of angioedema. Acute angioedema is frequently a direct consequence of the exposure to a specific substance (usually food, chemicals or drug) eliciting an allergic/pseudoallergic reaction, which releases histamine. Also, chronic recurrent angioedema, occurring with prominent urticarial flare, is typically histamine mediated. In contrast, for chronically recurrent angioedema without urticaria, the specific angioedema triggering is only vaguely described even when a predisposing condition is clearly identified. This situation is best illustrated in angioedema due to inherited C1-INH deficiency and in angioedema related to ACE inhibitor treatment. In spite of a lifelong stable C1-INH deficiency or of a continuous ACE inhibitor treatment, patients with these conditions are only occasionally symptomatic, with substantial variation in frequency and severity of symptoms.

The plasma kinin-forming pathway consists of three essential proteins that interact in vivo in a complex fashion once bound to a macromolecular complex formed during inflammatory response or bound to proteins along cell surfaces (Kaplan A. P., 2004. Mechanisms of bradykinin generation. In Urticaria and angioedema (Greaves, M. W. and A. P. Kaplan editors) (Marcel Decker Inc. New York) pp 51-72). These are coagulation factor XII [FXII (or Hageman Factor, HF)], prekallikrein (PK), and high molecular weight kininogen (HK). Once factor XII is activated to factor XIIa, it converts prekallikrein to kallikrein and the latter in turn digests HK to generate bradykinin. Factor XIIa has a second substrate in plasma; namely, coagulation factor XI and activation of surface bound factor XI by factor XIIa initiates the intrinsic coagulation pathway. Thus, the assembly and interactions of all four of these proteins are known as contact activation and the formation of bradykinin is therefore a cleavage product of the initiating step of the cascade (Kaplan, A. P. 2004. Mechanisms of bradykinin generation. In Urticaria and Angioedema, Greaves, M. W. and A. P. Kaplan editors, Marcel Decker Inc. New York, pp. 51-72). There is also a tissue pathway by which bradykinin is generated in which there is intracellular conversion of prekallikrein to tissue kallikrein by enzymes that are yet to be identified. Tissue kallikrein is secreted into the local milieu where it digests low molecular weight kininogen (LK) to generate lysyl-bradykinin (kallidin) and an amino-peptidase converts kallidin to bradykinin. The bradykinin that is produced by either pathway is then degraded by plasma enzymes as well as enzymes that are active along the surface of endothelial cells—particularly pulmonary vascular endothelial cells—to lower-molecular-weight peptides (Kaplan, 2004).

Bradykinin acts on the B2 receptor on the surface of the endothelial cells to cause vasodilatation and this in turn is enhanced by secondary production of vasodilators such as nitric oxide (NO) following stimulation of B2 receptors (Regoli & Barabe. 1980. Pharmacol. Rev. 32:1-46). In addition to its significant contribution to the inflammatory processes, the kinin-generating pathway has been implicated in various other physiological and pathophysiological processes including hypotension, tumor angiogenesis, and pain.

HK circulates in plasma as a 115 kDa non-enzymatic glycoprotein with a concentration of 70-90 µg/ml. Theoretically, there is sufficient concentration of HK in plasma to form non-covalent complexes with the two substrates of factor XIIa—prekallikrein and factor XI—thus leaving 10-20% of circulating HK uncomplexed. The attachment of prekallikrein or factor XI to HK occurs within the C-terminal region of HK, corresponding to the light chain that results after cleavage to release bradykinin. Earlier experiments have shown that the binding of HK to HUVECs (Kd 40-50 nM) is strictly zinc-dependent (25-50 mM), saturable, and reversible with an estimated $1 \times 10^6$ binding sites/cell. Furthermore, these experiments had shown that binding is with both the heavy and light chains of HK. Since there is apparently no separate site for prekallikrein, the prekallikrein-HK complex is brought to the endothelial cell surface by virtue of HK binding. When the binding of factor XII was studied, it was found to have binding characteristics strikingly similar to those seen with HK including a similar requirement for zinc. Subsequently, it was shown that HK and factor XII could compete for the same binding site at a comparable molar ratio suggesting that they compete for binding to the same or overlapping receptor sites.

Three endothelial cell binding sites for HK and factor XII have been described to date. These include gC1q-R, cytokeratin-1 (Hasan, et al., 1998. Proc. Natl. Acad. Sci. U.S.A. 95: 3615-3620; Joseph et al. 1999. Clin. Immunol. 92:246-255), and the urokinase plasminogen activator receptor (u-PAR) (Colman et al. 1997. J. Clin. Invest. 100:1481-1487). The binding of HK and factor XII to each of these proteins is zinc-dependent.

The HK binding site on gC1q-R has been identified on the C-terminal half corresponding to residues 204-218 (Ghebrehiwet et al. 1994. J. Exp. Med. 179:1809-1821; Ghebrehiwet et al. 2002. Immunobiol. 205:421-432. gC1q-R binds specifically to domain 5 in the light chain of HK but not to the heavy chain (Hasan et al. 1995. J. Biol. Chem. 270: 19256-19261; Herwald et al. 1996. J. Biol. Chem. 271:13040-13047). Domain 5 of HK, located within the N-terminus of the light chain, is rich in histidine and arginine residues and contains the site for interaction with gC1q-R. A 20 amino acid polypeptide termed HKH20 has been shown to be the site for attachment within domain 5 and this polypeptide can be used to inhibit the interaction of HK with intact endothelial cells (Hasan et al. 1995. J. Biol. Chem. 270: 19256-19261). The other site for attachment of HK to endothelial cells is found within domain 3 on the heavy chain, and a polypeptide containing the binding site, designated LDC27 has been identified. However, its binding affinity is approximately 100-fold less than the light chain (Herwald et al. 1995. J. Biol. Chem. 270:14634-14642).

The second endothelial cell-binding site for HK is cytokeratin 1. Like gC1q-R, this protein was isolated from cell membranes employing affinity chromatography with HK or LDC27 as ligand. Cytokeratin 1 therefore represents a major site of interaction for the HK heavy chain; although it is also capable of binding the light chain as well.

A third cell membrane constituent capable of binding HK is u-PAR, since antibody raised against u-PAR can inhibit cell membrane interaction with HK, and HK can bind to purified u-PAR in a zinc-dependent manner. Although purification of u-PAR using HK has not been successful, affinity chromatography using factor XII as ligand leads to purification of u-PAR rather selectively, with only traces of gC1q-R and cytokeratin-1 (Joseph et al. 2004. J. Thromb. Haemost. 91:61-70). Thus u-PAR may represent an important ligand for interaction with factor XII, while gC1q-R and cytokeratin-1 predominate in terms of HK binding. Because antibody to gC1q-R can immunoprecipitate gC1q-R and cytokeratin 1 but not u-PAR, and antibody to u-PAR can immunoprecipitate u-PAR and cytokeratin 1, but not gC1q-R, these molecules may reside on the membrane as closely associated bimolecular complexes of gC1q-R-cytokeratin-1 and u-PAR-cytokeratin-1 or as a trimolecular complex of gC1q-R-cytokeratin-1-u-PAR as was originally proposed (Joseph et al.; Mandi et al. 2001. Blood. 97:2342-2350; Mandi, et al. 2002. Hemost. Thromb. Vasc. Biol. 99:3585-3596).

Bradykinin and related kinins have been shown to induce vasodilatation and vascular permeability (Regoli & Barabe, 1980; Pharmacol. Rev 32: 1-46). When injected into humans and animals, bradykinin reproduces the cardinal signs and symptoms of inflammation, namely redness, local heat, swelling, and pain. Redness depends on endothelium-mediated vasodilatation, swelling from the contraction of capillary endothelia with the resulting opening of pores in the capillary filter, and pain from the stimulation of sensory fibers (Regoli & Barabe, 1980).

The biological effects of the kinins, including the stimulation of prostaglandin release, are mediated by two G-protein coupled receptors (GPCR) named B1 and B2 (Regoli & Barabe), which depending on the cell type in which they are expressed, promote the release of secondary mediators such as NO, PGI2, histamine and various neurotransmitters—all vasodilators and proinflammatory. Biological effects mediated by B1 and B2 receptors are linked to intracellular accumulation of Ca2+, cAMP, or cGMP. Whereas B2 receptors are constitutive, B1 receptors are inducible (by IL-1β, TNFα,) in pathological states.

The bradykinin that is produced during contact activation in vivo is degraded by plasma enzymes, as well as enzymes that are active along the surface of endothelial cells (particularly pulmonary vascular endothelial cells), to lower-molecular-weight peptides (Kaplan 2004). The major plasma enzyme is carboxypeptidase N, which removes the C-terminal arginine from bradykinin to yield an eight amino acid peptide, des-arg-9 bradykinin. The second kininase in plasma is termed kininase II, which predominates along the pulmonary vascular endothelial cell surface, and is identical to angiotensin-converting enzyme (ACE) (Yang, H Y T, Erdos, E G, 1967, Nature, 2151402-1403). This enzyme removes the dipeptide phe-arg from the C-terminus of bradykinin to yield a heptapeptide and a second cleavage removes ser-pro to leave a pentapeptide. Thus, bradykinin is controlled as soon as it is generated unless a condition(s) is created that favor its prolonged circulation in plasma. ACE inhibitors reduce catabolism of bradykinin.

The receptor for the globular heads of C1q, gC1q-R, is a ubiquitous, highly anionic cellular protein of 33 kDa that was identified and characterized as a cell-surface molecule that binds the globular heads of C1q (gC1q) (Ghebrehiwet et al. 1994. J. Exp. Med. 179: 1809-1821.-3). Known alternatively as p33, and sometimes as p32 or HABP-1 (hyaluronic acid binding protein I), it is now clear that it is also, and in fact predominantly, a protein of the mitochondrial matrix. In addition, it is distributed in several other cellular compartments, including the ER, and the nucleus, in addition to the cell surface (Ghebrehiwet et al. 1994. J. Exp. Med. 179: 1809-1821; Mandi et al. 2001. Blood. 97:2342-2350; Mandi et al. 2002. Hemost. Thromb. Vasc. Biol. 99:3585-3596). Binding of C1q to cells is known to induce and modulate a number of C1q-mediated cellular responses including inositol-trisphosphate (IP3) production in, expression of P-selectin on, and generation of procoagulant activity on, platelets; activation and expression of the adhesion molecules E-selectin, ICAM-1 and VCAM-1; and production of IL-6, IL-8, and monocyte chemoattractant protein-1 (MCP-1) on endothelial cells (ECs). Some of these functions have been shown by antibody inhibition to directly involve gC1q-R and/or the receptor for the collagen-like domains of C1q, cC1q-R/CR. In addition, gC1q-R in association with u-PAR and cytokeratin 1, is a high-affinity site for HK (Colman et al. 1997. J. Clin. Invest. 100:1481-1487; Hasan, et al. 1998. Proc. Natl. Acad. Sci. U.S.A. 95: 3615-3620).

One of the major side effects of patients on ACE inhibitors is angioedema (Agah et al. 1999. Intensive Care Med 23: 793-796; Agostoni et al. 1999. Immunopharmacology 15:21-25). ACE inhibitor-mediated angioedema has been reported to occur in 0.1-5.0% of patients, being five times more common in Afro-Caribbean Americans, and appears to be indistinguishable from any other form of angioedema. This type of angioedema, whose features include odynophagia (retrosternal pain with swallowing), swelling of the tongue, and potentially lethal laryngeal edema, has been reported to be a frequent cause (17-38%) of acute angioedema in referral centers today (Agah et al. 1999. Intensive Care Med 23: 793-796; Agostoni et al. 1999. Immunopharmacology 15:21-25). The present invention provides methods for treating and/or preventing angioedema and vascular permeability by interfering primarily with the interaction of HK with gC1q-R, and secondarily with the interaction of C1q with gC1qR.

SUMMARY OF THE INVENTION

The present invention provides a method of treating or preventing angioedema in a patient in need thereof comprising administering to the patient a therapeutically effective amount of an agent that inhibits the interaction of HK with gC1q-R. The invention also provides a method of treating or preventing angioedema in a patient in need thereof comprising administering to the patient an effective amount of an agent that inhibits the interaction of C1q with gC1q-R. In an embodiment of the invention, the agent inhibits the interaction of HK and C1q with gC1q-R. The present invention also provides a method of treating or preventing vascular permeability in a patient in need thereof comprising administering to the patient a therapeutically effective amount of an agent that inhibits the interaction of HK and/or C1q with gC1q-R.

The present invention provides a method of modulating HK binding to gC1q-R comprising administering to a patient in need thereof an effective amount of an agent that inhibits the interaction of HK with gC1q-R. The present invention also provides a method of modulating C1q binding to gC1q-R comprising administering to a patient in need thereof an effective amount of an agent that inhibits the interaction of C1q with gC1q-R. In an embodiment of the invention, the agent inhibits the interaction of HK and C1q with gC1q-R. In one embodiment, the patient produces elevated amounts of bradykinin. In another embodiment, bradykinin degradation in the patient is reduced. In one embodiment the patient is taking an angiotensin converting enzyme (ACE) inhibitor.

In one embodiment the agent comprises an antibody or polypeptide. In another embodiment the agent comprises an antibody that binds to an HK-binding site of gC1q-R. In another embodiment the antibody is mAb 74.5.2, mAb 83.1, or mAb 48. In another embodiment the antibody binds to a gC1q-R binding site of HK. In another embodiment the agent comprises a polypeptide selected from the group consisting of SEQ ID NO NO:1, SEQ ID NO NO:2, SEQ ID NO NO:3, SEQ ID NO:4, SEQ ID NO:5, SEQ ID NO:6, SEQ ID NO:7, SEQ ID NO:8, SEQ ID NO:9, and SEQ ID NO:10, and combinations thereof. In another embodiment the agent comprises a small polypeptide molecule derived from domain 5 of HK, for example SEQ ID NO:11, SEQ ID NO:12, SEQ ID NO:13, and SEQ ID NO:14, and combinations thereof.

The invention also provides pharmaceutical compositions for treating or preventing angioedema or vascular permeability in a patient in need thereof comprising a therapeutically effective amount of an agent that is capable of inhibiting the interaction of HK with gC1q-R. In one embodiment the agent comprises an antibody or polypeptide. In one embodiment, the pharmaceutical composition is administered along with an ACE inhibitor, either simultaneously or sequentially.

The invention also provides a method for identifying an agent for treating or preventing angioedema or vascular permeability comprising testing the agent for its ability to prevent the interaction of HK with gC1q-R.

BRIEF DESCRIPTION OF THE FIGURES

FIG. 5. Panel A: Solution phase HKH20 inhibits binding of gC1q-R to microtiter bound HKH. ELISA wells were first coated with 50 µg/ml peptide HKH20 (SEQ ID NO:11). The wells were then incubated either with biotinylated gC1q-R (5 µg/ml) alone (lane 2) or in the presence of 10 µg/ml (lane 3) or 50 µg/ml (lane 4) HKH20. Lane 3 was coated with biotinylated gC1q-R (1 µg/ml) and detected with alkaline-phosphatase conjugated NeutrAvidin. The figure is a representative of two experiments done in duplicate. Co-crystallography of HKH-20 with gC1q-R, while successful, had a weak resolution at 4 Å instead of the desired 2.5 Å. Panel B: HKH20 and histidine-rich fragments bind to gC1q-R. Binding of gC1q-R to HKH-20 (SEQ ID NO:11), HKH-10-1 (residues 479-488; SEQ ID NO:13), HKH-10-2 (residues 484-493; SEQ ID NO:14), and HKH-10-3 (residues 489-498; SEQ ID NO:15). The negative control is binding to BSA.

DETAILED DESCRIPTION OF THE INVENTION

One aspect of the present invention provides a method of treating or preventing angioedema in a patient in need thereof comprising administering to the patient a therapeutically effective amount of an agent that is capable of inhibiting the interaction of HK with gC1q-R. The present invention also provides a method of treating or preventing vascular permeability in a patient in need thereof comprising administering to the patient a therapeutically effective amount of an agent that is capable of inhibiting the interaction of HK with gC1q-R.

The complement and the kinin/kallikrein systems play a major role in the initiation and/or exacerbation of inflammatory processes associated with various diseases including angioedema, infection and cancer. Because gC1q-R can activate both pathways to release vasoactive peptides, soluble or cell surface-expressed gC1q-R can contribute to the inflammatory process by modulating complement activation, kinin generation and perhaps even initiation of clotting via contact system. This is particularly true in the vasculature, where atherogenic factors (e.g. immune complexes, bacteria or virus) are perceived not only to convert the endothelium into a procoagulant and proinflammatory surface, but also to induce enhanced expression of cell surface molecules such as gC1q-R. Ghebrehiwet et al, 2006; In Current Topics in Complement, 95-105).

Angioedema

Angioedema (AE) is a condition characterized by significant localized swelling of deeper layers of the skin, mucosa, or submucosal tissues. Angioedema is readily recognized as an usually asymmetrical, non-erythematous, non-pruritic, non-pitting, localized, transient, episodic swelling of a soft body area involving lax skin, oropharyngolaryngeal tissue and/or gastrointestinal wall. It affects at least 20% of the population and several forms recur chronically, causing significant personal, domestic, social, and occupational disability. The processes and signs underlying the lesions of angioedema are typical of the inflammatory process; but increased vascular permeability predominates, leading to massive dermal and subcutaneous edema, becoming particularly life threatening if it occurs in the upper respiratory tract. Angioedema can be related to a large number of factors that may act as direct triggers (e.g., allergic/pseudoallergic reactions to food and drugs) or as predisposing conditions (e.g., inherited or acquired deficiencies of C1-INH, ACE inhibitor treatment).

Vascular Permeability

Vascular permeability is the characteristic permitting the passage of liquids, small molecules, or cells through the blood vessel wall (i.e., from the lumen to the tissue). Vascular permeability may be estimated by monitoring the transport of systemically injected tracers, such as tetramethyl-rhodamine-labelled albumin, by intravital microscopy.

Vascular permeability can be measured using a transwell model of vascular leakage—measuring the permeability of FITC-BSA through endothelial cells (ECs), isolated from human umbilical vein (HUVEC), grown to confluence on an insert and exposed to 10% human citrated plasma. The amount of FITC-BSA that passes through the EC monolayers, and is thus found in the lower chamber, is measured by a fluorometer at different time points.

For example, plasma from C1-INH deficient patients, collected during an angioedema attack (henceforth referred to as attack plasma) and during remission, is tested using a transwell model of vascular leakage with plasma pooled from healthy donors serving as a control. Negligible levels of FITC-BSA can be detected when ECs are incubated for 30 minutes with medium or medium supplemented with plasma from controls or from patients in remission. Conversely, a two to three-fold increase in the FITC-BSA level can be found in the bottom well when the cells were exposed to attack plasma. This indicates that endothelial cells are directly involved in the vascular leakage obtained with the plasma of C1-INH deficient patients and should not be considered simply a passive target of these factors.

Using a transwell model for vascular leakage, examination of the kinetics of leakage shows that the enhanced permeability peaks 30 minutes after exposure to attack plasma obtained from patients with acquired angioedema or with hereditary angioedema. HUVEC monolayers were incubated either with 10% plasma obtained from patients during attack or remission or with 10% plasma obtained from four blood donors or bradykinin (BK) ($10^{-6}$ M) for 30 min at 37° C. FITC-BSA that leaked into the lower chamber was collected and measured using an Infinite200 fluorometer. Bradykinin was used as a positive control and caused a rapid (<5 min) increase in leakage.

Additional information was also obtained by experiments in which ECs were first incubated with the attack phase plasma of one of these patients for 30 min and then testing the supernatant of this incubation for its permeabilizing activity in another transwell. A rapid flux of FITC-BSA, essentially similar to that induced by bradykinin, was observed within 5 minutes after addition of the supernatant.

Inhibiting the Interaction of HK and/or C1q with gC1q-R

Agents of the present invention are based on the recognition that HK and C1q are involved in the generation of angioedema. Therefore agents that inhibit the interaction of HK with gC1q-R or C1q with gC1q-R would be considered therapeutic agents. Agents may include an antibody, a polypeptide, a nucleic acid, a small molecule, or any other suitable antagonist of the interaction. The agents are sufficient to block binding, completely or partially, at a therapeutically acceptable dose.

The in vivo effectiveness of these agents can be tested using in vitro or in vivo model systems such as the rat or hamster using intravital microscopy wherein, bradykinin, or attack phase plasma from angioedema patients is used to induce angioedema and effects are monitored by injecting an appropriate tracer such as BSA-FITC. Bacterial invasion can also generate bradykinin, presumably as an escape mechanism to cause septicemia. Using rats or hamster animal models of endocarditis and infection, we have, in fact, shown that the dissemination of *Staphylococcus aureus* to distant target organs is significantly inhibited by mAb 74.5.2.

Treatment and Prophylaxis

The terms "ameliorate" and "treat" are used interchangeably and include both therapeutic treatment and prophylactic treatment (reducing the likelihood of development). Both terms mean decrease, suppress, attenuate, diminish, arrest, or stabilize the development or progression of a disease (e.g., a disease or disorder delineated herein), lessen the severity of the disease or improve the symptoms associated with the disease. They should not be taken to imply that a subject is treated to a total recovery.

The invention provides a method of treating or preventing angioedema in a subject in need thereof. The angioedema can be hereditary, acquired, or allergy-related. The angioedema can also be related to a drug treatment or therapy. For example, angioedema affects a subset of patients being treated with an angiotensin converting enzyme (ACE) inhibitor (e.g., for treatment of hypertension), and ACE inhibition has been observed to block bradykinin degradation. Angioedema is also observed in conditions and treatments that lead to elevated levels of bradykinin precursors. For example, patients undergoing fibrinolytic treatment for ischemic stroke with recombinant tissue plasminogen activator (rtPA) have elevated plasma kallikrein and an elevated incidence of angioedema.

Urticaria and angioedema are inflammatory dermal processes. The lesions of urticaria, which are redness, warmth and edema, are caused by localized vasodilatation that leads to swelling or edema. Similar processes underlie angioedema, but in this case vascular permeability predominates leading to massive dermal and subcutaneous edema (Sabroe, A R. and M W Greaves. 2004. What is urticaria? Anatomical, physiological and histological considerations and classification. In Urticaria and angioedema (Greaves M W and A P Kaplan editors) pp. 1-18).

Antibodies

In one embodiment, the methods and compositions of the present invention comprise one or more antibodies that bind to an HK binding site of gC1q-R, for example binding to all or part of the region from about amino acid 190 to about amino acid 218 of the gC1q-R protein. In another embodiment the antibody binds within a gC1q-R binding site of HK, for example binding within about amino acid 212 to about amino acid 223 of the gC1q-R protein. Similarly, one or more antibodies that bind to a C1q binding site of gC1q-R, for example binding to all or part of the region from about amino acid 76 to about amino acid 93 of the gC1q-R protein. The complete nucleotide and amino acid sequences of human gC1q-R can be found under GenBank accession number NM_001212.3 (GI:28872801). The complete nucleotide and amino acid sequences of HK can be found under GenBank accession number NM_001102416.1 (GI:156231036).

Antibodies of the invention include those consisting of heavy and light chains in their natural configuration, and functional fragments or modifications thereof. The antibodies of the present invention may be monoclonal or polyclonal raised in animals, but can also be humanized, super-humanized, or chimeric antibodies, or human antibodies. The term monoclonal antibody as used herein refers to an antibody obtained from a substantially homogeneous population of antibodies. The antibodies within the population are identical, except for possible mutations occurring in a small subset of the antibodies. As used herein, monoclonal antibodies include chimeric antibodies, in which constant regions are obtained from one source and variable regions from a different source, humanized antibodies in which all but the complementarity determining regions (CDRs) are human, and "superhuman" antibodies in which human CDRs are incorporated into human variable domains. Antibodies that can be used according to the invention include complete immunoglobulins, antigen binding fragments of immunoglobulins, as well as antigen binding proteins that comprise antigen-binding domains of immunoglobulins. Antigen binding fragments of immunoglobulins include, for example, Fab, Fab', and F(ab')$_2$. Other antibody formats have been developed which retain binding specificity, but have other characteristics that may be desirable, including for example, bi-specificity, multi-valence (more than two binding sites), compact size (e.g., binding domains alone).

Naturally occurring antibodies typically have two identical heavy chains and two identical light chains, with each light chain covalently linked to a heavy chain by an interchain disulfide bond. Multiple disulfide bonds further link the two heavy chains to one another. Individual chains can fold into domains having similar sizes (110-125 amino acids) and structures, but different functions. The light chain can comprise one variable domain (VL) and/or one constant domain (CL). The heavy chain can also comprise one variable domain (VH) and/or, depending on the class or isotype of antibody, three or four constant domains ($C_H1$, $C_H2$, $C_H3$ and $C_H4$). In humans, the isotypes are IgA, IgD, IgE, IgG, and IgM, with IgA and IgG further subdivided into subclasses or subtypes (IgA1-2 and IgG1-4).

Generally, the variable domains show considerable amino acid sequence variability from one antibody to the next, particularly at the location of the antigen-binding site. Three regions, called hypervariable or complementarity-determining regions (CDRs), are found in each of VL and VH, which are supported by less variable regions called framework variable regions.

The portion of an antibody consisting of VL and VH domains is designated Fv (fragment variable) and constitutes the antigen-binding site. Single chain Fv (scFv) is an antibody fragment containing a VL domain and a VH domain on one polypeptide chain, wherein the N terminus of one domain and the C terminus of the other domain are joined by a flexible linker (see, e.g., U.S. Pat. No. 4,946,778 (Ladner et al.); WO 88/09344, (Huston et al.). WO 92/01047 (McCafferty et al.) describes the display of scFv fragments on the surface of soluble recombinant genetic display packages, such as bacteriophage.

Single chain antibodies lack some or all of the constant domains of the whole antibodies from which they are derived. Therefore, they can overcome some of the problems associated with the use of whole antibodies. For example, single-chain antibodies tend to be free of certain undesired interactions between heavy-chain constant regions and other biological molecules. Additionally, single-chain antibodies are considerably smaller than whole antibodies and can have greater permeability than whole antibodies, allowing single-chain antibodies to localize and bind to target antigen-binding sites more efficiently. Furthermore, the relatively small size of single-chain antibodies makes them less likely to provoke an unwanted immune response in a recipient than whole antibodies.

Multiple single chain antibodies, each single chain having one VH and one VL domain covalently linked by a first polypeptide linker, can be covalently linked by at least one or more peptide linker to form a multivalent single chain antibodies, which can be monospecific or multispecific. Each chain of a multivalent single chain antibody includes a variable light chain fragment and a variable heavy chain fragment, and is linked by a polypeptide linker to at least one other chain. The polypeptide linker is composed of at least fifteen amino acid residues. The maximum number of amino acid residues is about one hundred.

Two or more single chain antibodies can be constructed so as to associate into complexes having more than one antigen-binding site. For example, two chains can be combined to form a diabody (i.e., a bivalent dimer). Diabodies have two binding sites, and can be monospecific or bispecific. Each chain of the diabody includes a VH domain joined to a VL domain with a linker short enough to prevent pairing between domains on the same chain. Thus, complementary domains on different chains pair with one another to recreate the two antigen-binding sites. Similarly, three chains can be combined to form a triabody. Triabodies are constructed with the amino acid terminus of a VL or VH domain directly fused to the carboxyl terminus of a VL or VH domain, i.e., without any linker sequence. The triabody has three Fv heads with the polypeptides arranged in a cyclic, head-to-tail fashion. A possible conformation of the triabody is planar with the three binding sites located in a plane at an angle of 120 degrees from one another. Triabodies can be monospecific, bispecific or trispecific.

Fab (Fragment, antigen binding) refers to the fragment of an antibody consisting of VL, CL, VH, and CH1 domains. Such fragments can be generated by papain digestion of an antibody, or expressed from nucleic acids encoding those domains. F(ab')$_2$ refers to the fragment of an antibody obtained by digestion with pepsin. F(ab')$_2$ antibody fragments also contain VL, CL, VH, and CH1 domains, as well as a heavy chain hinge region through which dimers are formed. Such fragments can also be generated using recombinant DNA techniques.

Fc (Fragment crystallization) is the designation for the portion or fragment of an antibody that comprises paired heavy chain constant domains. In an IgG antibody, for example, the Fc comprises $C_H2$ and $C_H3$ domains. The Fc of an IgA or an IgM antibody further comprises a $C_H4$ domain. The Fc is associated with Fc receptor binding, activation of complement-mediated cytotoxicity, and antibody-dependent cellular-cytoxicity (ADCC). For antibodies such as IgA and IgM, which are complexes of multiple IgG like proteins, antibody formation requires Fc constant domains.

Specificity of antibodies, or fragments thereof, can be determined based on affinity and/or avidity. Affinity, represented by the equilibrium constant for the dissociation of an antigen with an antibody (Kd), measures the binding strength between an antigenic determinant and an antibody-binding site. Avidity is the measure of the strength of binding between an antibody with its antigen. Avidity is related to both the affinity between an epitope with its antigen-binding site on the antibody, and the valence of the antibody, which refers to the number of antigen binding sites of a particular epitope. Antibodies typically bind with a dissociation constant (Kd) of $10^{-5}$ to $10^{-11}$ liters/mol. Any Kd less than $10^{-4}$ liters/mol is generally considered to indicate nonspecific binding. The lesser the value of the Kd, the stronger the binding strength between an antigenic determinant and the antibody-binding site.

As used herein, "antibodies" and "antibody fragments" includes modifications that retain specificity for a specific antigen. Such modifications include, but are not limited to, conjugation to an effector molecule such as a chemotherapeutic agent (e.g., cisplatin, taxol, doxorubicin) or cytotoxin (e.g., a protein, or a non-protein organic chemotherapeutic agent). The antibodies can be modified by conjugation to detectable reporter moieties. Also included are antibodies with alterations that affect non-binding characteristics such as half-life (e.g., pegylation).

Proteins and non-protein agents may be conjugated to the antibodies by methods that are known in the art. Conjugation methods include direct linkage, linkage via covalently attached linkers, and specific binding pair members (e.g., avidin-biotin). Such methods include, for example, that described by Greenfield et al., Cancer Research 50:6600-6607 (1990) for the conjugation of doxorubicin and those described by Arnon et al., Adv. Exp. Med. Biol. 303, 79-90 (1991) and by Kiseleva et al., Mol. Biol. (USSR) 25:508-514 (1991) for the conjugation of platinum compounds.

Antibodies and antibody fragments of the present invention further include those for which binding characteristics have been improved by direct mutation, methods of affinity maturation, phage display, or chain shuffling. Affinity and specificity can be modified or improved by mutating CDRs and screening for antigen binding sites having the desired characteristics (see, e.g., Yang et al., J. Mol. Biol., 254: 392-403 (1995)). CDRs are mutated in a variety of ways. One way is to randomize individual residues or combinations of residues so that in a population of otherwise identical antigen binding sites, all twenty amino acids are found at particular positions. Alternatively, mutations are induced over a range of CDR residues by error prone PCR methods (see, e.g., Hawkins et al., J. Mol. Biol., 226: 889-896 (1992)). For example, phage display vectors containing heavy and light chain variable region genes can be propagated in mutator strains of *E. coli* (see, e.g., Low et al., J. Mol. Biol., 250: 359-368 (1996)). These methods of mutagenesis are illustrative of the many methods known to one of skill in the art.

Each domain of the antibodies of this invention can be a complete immunoglobulin domain (e.g., a heavy or light chain variable or constant domain), or it can be a functional equivalent or a mutant or derivative of a naturally-occurring domain, or a synthetic domain constructed, for example, in vitro using a technique such as one described in WO 93/11236 (Griffiths et al.). For instance, it is possible to join together domains corresponding to antibody variable domains, which are missing at least one amino acid. The important characterizing feature of the antibodies is the presence of an antigen binding site. The terms variable heavy and light chain fragment should not be construed to exclude variants that do not have a material effect on specificity.

Antibodies of the present invention can be obtained by any technique, for example, from naturally occurring antibodies, or Fab or scFv phage display libraries. It is understood that, to make a single domain antibody from an antibody comprising a VH and a VL domain, certain amino acid substitutions outside the CDRs can be desired to enhance binding, expression or solubility. For example, it can be desirable to modify amino acid residues that would otherwise be buried in the VH-VL interface.

Antibodies of the invention can be obtained by standard hybridoma technology (Harlow & Lane, ed., Antibodies: A Laboratory Manual, Cold Spring Harbor, 211-213 (1988), which is incorporated by reference herein). Human monoclonal antibodies can be made, for example, by priming of B cells and fusion to create a heterohybrid (Boerner et al., 1991, J. Immunology., 147(1):86-95), or by EBV transformation of human B cells (Traggiai et al., 2004, Nat. Med. 10:871-5), and the binding characteristics of such antibodies and be modified or improved by in vitro (See, Li et al., 2006, Proc. Natl. Acad. Sci. USA 103:3557-62). Human monoclonal antibodies can also be obtained from transgenic mice that produce human immunoglobulin gamma heavy and kappa light chains (e.g., KM mice from Medarex, San Jose, Calif.). In one embodiment, a substantial portion of the human antibody producing genome is inserted into the genome of the mouse, and is rendered deficient in the production of endogenous murine antibodies. Such mice may be immunized subcutaneously (s.c.) with part or all of target molecule in complete Freund's adjuvant. Human antibodies can also be developed using phage display techniques (See, e.g., Hoogenboom et al., 1991, J. Mol. Biol. 227:381; Marks et al., 1991, J. Mol. Bio. 222:581).

Polypeptide and Polypeptide-Like Agents

In one aspect of the invention, the agent that inhibits the interaction of HK with gC1q-R is a polypeptide molecule that blocks or inhibits the interaction of HK with gC1q-R. The polypeptides can be synthesized specifically or selected from a pool using various screening methods known in the art for example a yeast two-hybrid system. In one embodiment the polypeptide agent binds to a HK binding site on gC1q-R. In another embodiment the polypeptide agent binds to a gC1q-R binding site on HK. In one embodiment the agent comprises a polypeptide selected from the group consisting of SEQ ID NO:1, SEQ ID NO:2, SEQ ID NO:3, SEQ ID NO:4, SEQ ID NO:5, SEQ ID NO:8, SEQ ID NO:9, SEQ ID NO:10, SEQ ID NO:11, SEQ ID NO:12, SEQ ID NO:13, and SEQ ID NO:14. In another embodiment the agent comprises a small polypeptide molecule derived from domains 5 and 6 of HK, for example SEQ ID NO:11, SEQ ID NO:13, or SEQ ID NO:14.

Useful polypeptides can also be identified by screening of libraries. Such polypeptides are generally 30 amino acids or less, and can be, for example, from 4 to 20 amino acids, or from 5 to 15 amino acids, or from 7 to 10 amino acids. The structure of the polypeptides can be constrained, for example by disulfide bonds between included cysteine residues, and can be cyclic.

Other types of libraries may also be employed, for example, any sort of synthetic polymers that can be screened and optionally, their structure or sequence determined. Numerous methods have been devised for generation of chemical diversity and mass screening of libraries. To simplify identification of library elements of interest, many libraries have the feature that synthesis steps are encoded. For example, in phage display, the displayed peptide is encoded in the genome encapsulated by the phage particle. Amino acid sequences of peptides identified by screening procedures are easily determined by sequencing a small predetermined part of the genome.

In another example, it has been demonstrated that peptides can be generated in numbers several orders of magnitude greater than by conventional one-at-a-time methods by synthesis on polyethylene rods or pins, arranged, for example, in a microtiter plate format. The pin technology is representative of techniques that generate libraries of single compounds in a spatially-differentiated manner. An alternative approach, to rapidly prepare large mixtures of compounds, is the split-pool approach (e.g., Houghten, R. A., 1985, Proc. Natl. Acad. Sci. U.S.A., 82:5131-5135) where a solid support material (e.g., beads) is physically segregated into equal portions for coupling to each of the individual initial reactants. This affords uniform coupling since competition between reactants is eliminated. The individual polymers are combined in a single vessel for washing and deprotection and then divided again into individual portions for the next coupling. Using this approach, a complete set of possible molecular combinations is rapidly prepared in approximately equimolar amounts. Coincident with coupling reactions, "identifier" tags can be attached to the solid support material. The structure of the molecule on any bead identified through screening is obtained by decoding the identifier tags. Numerous methods of tagging the beads have now been reported.

Inhibitors further include polymers of peptide-like molecules, and libraries of such molecules can be screened in the manner of antibodies and peptides. Such molecules are well known in the art, including but not limited to, D-peptides and peptoids. D-peptides are polypeptides that contain D-amino acids. Peptoid libraries are a collection of N-substituted glycines as peptoid monomers which are assembled in a modular fashion. (Zuckermann, R. N. et al, 1994, J. Med. Chem. 37:2678-2685.) The structures of the resulting compounds are unique, display unique binding properties, and incorporate the important functionalities of peptides in a novel backbone. Furthermore, studies suggest this class of compounds is resistant to enzymatic breakdown.

In one aspect of the invention, the agent that inhibits the interaction of HK with gC1q-R may be an aptamer, which are oligonucleic acid molecules that bind a specific target molecule. They can be synthesized specifically or selected from a pool using various screening methods known in the art for example a yeast two-hybrid system.

In one embodiment, the agent that inhibits the interaction of HK with gC1q-R may mimic binding of HK to gC1q-R or binding of gC1q-R to HK.

Small Molecules

In one aspect of the invention, the agent that is effective of inhibiting the interaction of HK with gC1q-R may be a small molecule. In this context, the term small molecule refers to small organic compounds, such as heterocycles, peptides, saccharides, steroids, and the like. The small molecule modulators preferably have a molecular weight of less than about 1500 Daltons, and more preferably less than about 500 Daltons. The compounds may be modified to enhance efficacy, stability, pharmaceutical compatibility, and the like. Candidate inhibitor compounds can be screened from libraries of synthetic or natural compounds. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). Combinatorial libraries are available or can be prepared according to known synthetic techniques. Alternatively, libraries of natural compounds in the form of bacterial, fungal, plant and animal extracts are available from e.g., Pan Laboratories (Bothell, Wash.) or MycoSearch (NC), or are readily producible by methods well known in the art. Additionally, natural and synthetically produced libraries and compounds may be further modified through conventional chemical and biochemical techniques.

Pharmaceutical Composition

A therapeutically effective amount of the pharmaceutical composition of the present invention is sufficient to treat and/or prevent angioedema or vascular permeability. The dosage of active agent(s) may vary, depending on the reason for use and the individual subject. The dosage may be adjusted based on the subject's weight, the age and health of the subject, and tolerance for the compound or composition.

In another aspect, the present invention provides pharmaceutically acceptable compositions which comprise a therapeutically effective amount of an agent effective at treating or preventing angioedema and/or vascular permeability, formulated together with one or more pharmaceutically acceptable excipients. The active agent and excipient(s) may be formulated into compositions and dosage forms according to methods known in the art. The pharmaceutical compositions of the present invention may be specially formulated for administration in solid or liquid form, including those adapted for the following: (1) oral administration, for example, tablets, capsules, powders, granules, pastes for application to the tongue, aqueous or non-aqueous solutions or suspensions, drenches, or syrups; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The phrase "pharmaceutically-acceptable excipient" as used herein refers to a pharmaceutically-acceptable material, composition or vehicle, such as a liquid or solid filler, diluent, carrier, manufacturing aid (e.g., lubricant, talc magnesium, calcium or zinc stearate, or steric acid), solvent or encapsulating material, involved in carrying or transporting the therapeutic compound for administration to the subject. Each excipient should be "acceptable" in the sense of being compatible with the other ingredients of the formulation and not injurious to the patient. Some examples of materials which can serve as pharmaceutically-acceptable excipients include: sugars, such as lactose, glucose and sucrose; starches, such as corn starch and potato starch; cellulose and its derivatives, such as sodium carboxymethyl cellulose, ethyl cellulose and cellulose acetate; gelatin; talc; waxes; oils, such as peanut oil, cottonseed oil, safflower oil, sesame oil, olive oil, corn oil and soybean oil; glycols, such as ethylene glycol and propylene glycol; polyols, such as glycerin, sorbitol, mannitol and polyethylene glycol; esters, such as ethyl oleate and ethyl laurate; agar; buffering agents; water; isotonic saline; pH buffered solutions; and other non-toxic compatible substances employed in pharmaceutical formulations. If desired, certain sweetening and/or flavoring and/or coloring agents may be added. Other suitable excipients can be found in standard pharmaceutical texts, e.g. in "Remington's Pharmaceutical Sciences", The Science and Practice of Pharmacy, 19th Ed. Mack Publishing Company, Easton, Pa., (1995).

Excipients are added to the composition for a variety of purposes. Diluents increase the bulk of a solid pharmaceutical composition, and may make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the subjects's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

In liquid pharmaceutical compositions of the present invention, the active agent and any other solid excipients are dissolved or suspended in a liquid carrier such as water, water-for-injection, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste. Flavoring agents and flavor enhancers may make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol and tartaric acid.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as gluconic acid, lactic acid, citric acid or acetic acid, sodium gluconate, sodium lactate, sodium citrate or sodium acetate. Selection of excipients and the amounts used may be readily determined by the formulation scientist based upon experience and consideration of standard procedures and reference works in the field.

Solid and liquid compositions may also be dyed using any pharmaceutically acceptable colorant to improve their appearance and/or facilitate patient identification of the product and unit dosage level.

The dosage form of the present invention may be a capsule containing the composition, for example, a powdered or granulated solid composition of the invention, within either a hard or soft shell. The shell may be made from gelatin and optionally contain a plasticizer such as glycerin and sorbitol, and an opacifying agent or colorant.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling may include any of the aforementioned blends and granulates that were described with reference to tableting, however, they are not subjected to a final tableting step.

The composition of the invention may be administered alone or may be administered in combination with one or more of other therapeutic agents. In one embodiment the composition of the present invention is administered in combination with an ACE inhibitor.

The term "patient" as used herein refers to any organism in need of treatment, or requiring preventative therapy, for angioedema or vascular permeability with the methods and compositions of the invention. The patient may be livestock, such as cattle, swine, sheep, poultry, and horses, or pets, such as dogs and cats. The patient may also be a human.

All references referred to herein are incorporated in their entirety.

EXAMPLES

Example 1

Kallikrein is Generated from gC1q-R

Figure 1:
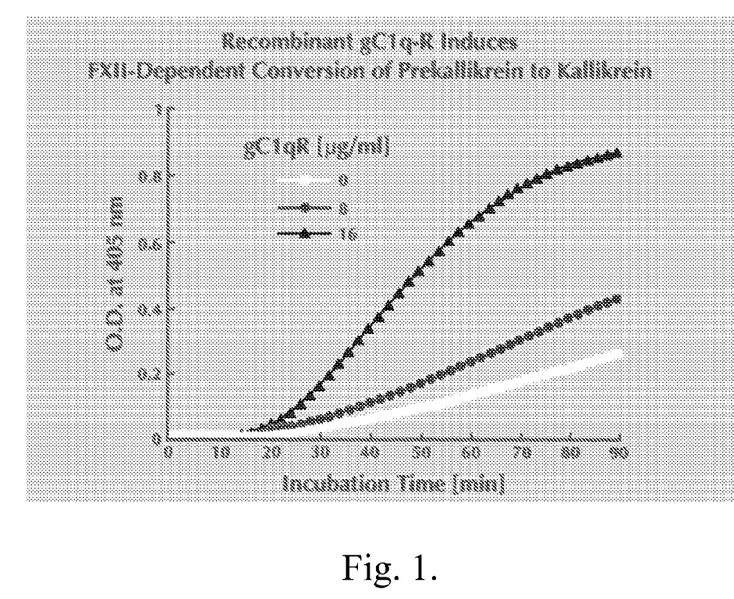
FIG. 1 shows results of a representative experiment in which the enzyme, kallikrein, which converts HK to bradykinin is generated by gC1q-R.

Kinins generated from the activation of the complement and/or contact systems have been implicated in the vascular leakage associated with C1 inhibitor (C1-INH) deficiency. A transwell model for vascular leakage was used to demonstrate that endothelial cells, and in particular gC1q-R on the endothelial cells, are directly involved in the vascular leakage obtained with the plasma of C1-INH deficient patients. The vascular leakage results from the assembly and the generation of bradykinin by the enzyme kallikrein. As shown in FIG. 1, the assembly of contact activation proteins on gC1q-R results in the generation of kallikrein.

Example 2

Activation of Complement by gC1q-R

Figure 2:
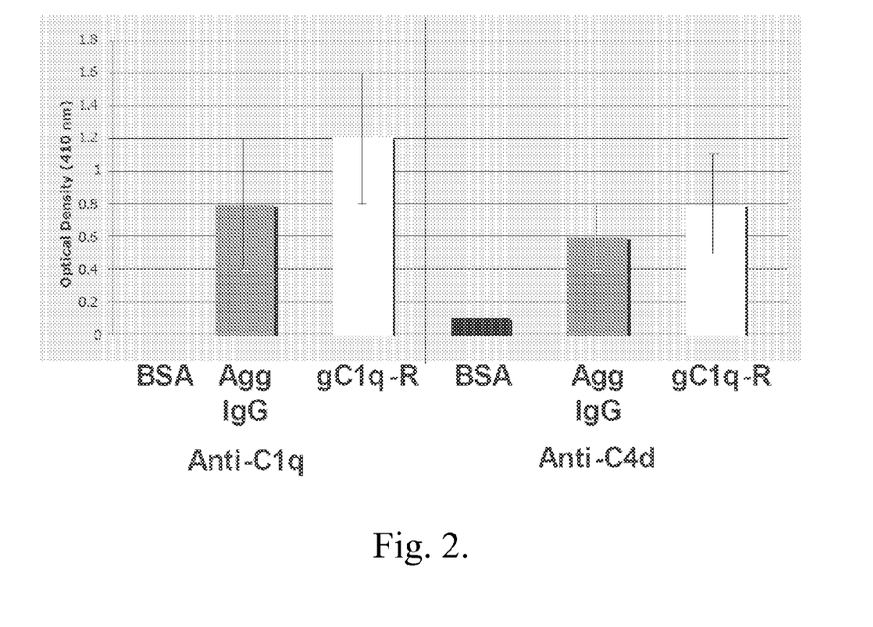
FIG. 2 provides evidence that the serum complement system is activated on microtiter coated gC1q-R and is similar in its potency to results obtained by immune complexes or aggregated IgG, both of which are potent activators of the complement.

Because gC1q-R recognizes the same or overlapping sites on C1q, which is also recognized by immune complexes, gC1q-R has the capacity to activate the classical pathway of complement. In the example (FIG. 2), microtiter wells were coated with either irrelevant control antigen (BSA), aggregated IgG (positive control) or gC1q-R. Then normal human serum diluted (1:10), was added and after 1 h incubation, the binding of C1q and the generation of C4d, a complement activation fragment was measured. Since the classical pathway of complement is activated by the binding of this molecule to activating complexes or surfaces, the presence of C1q proves that the classical pathway was indeed activated.

Example 3

Identification of Monoclonal Antibodies that Block HK

Figure 3:
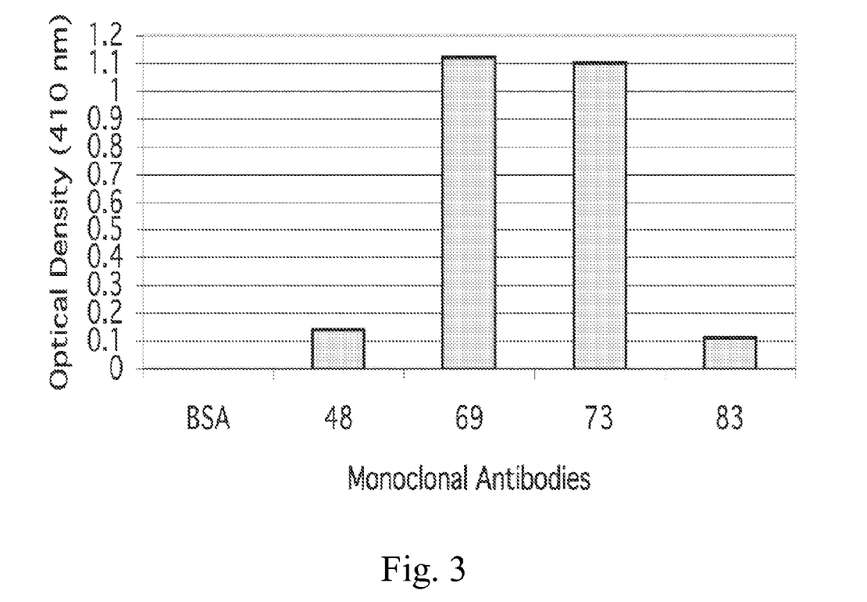
FIG. 3 documents the identification of two novel antibodies-mAb 48 and mAb 83-which block binding of HK to gC1q-R at residues 190-202 (SEQ ID: 5) representing a secondary binding site.

By peptide mapping and antibody inhibition studies, we have previously identified a binding site for HK in a gC1q-R domain contained within residues 204-218. However, although mAb 74.5.2, which recognizes residues 204-218, can inhibit HK and FXII binding, the inhibition is not complete suggesting the existence of other sites. Thus a possible binding site(s) elsewhere in the molecule was sought. Several peptides were synthesized that correspond with the gC1q-R domains of very high negative charge and, which based on their location in the crystal structure on the solution-face, are hypothesized to interact with solution-phase ligands. When the peptides were tested by solid phase ELISA for their ability to support HK binding, a gC1q-R peptide (amino acids 190-202) strongly supported binding of HK. These data were confirmed by performing capture studies from diluted plasma (1:10, in TBS). HK was bound to wells coated with peptide 190-202 and was detected by a monoclonal antibody to HK. Furthermore, two monoclonal antibodies, mAb 48 and 83, were identified which not only recognize residues 190-202 but also inhibit HK binding (FIG. 3). These antibodies have now been isotyped to be IgG1k.

Example 4

Monoclonal Antibody 74.5.2 but not 60.11 Blocks Vascular Permeability

Figure 4:
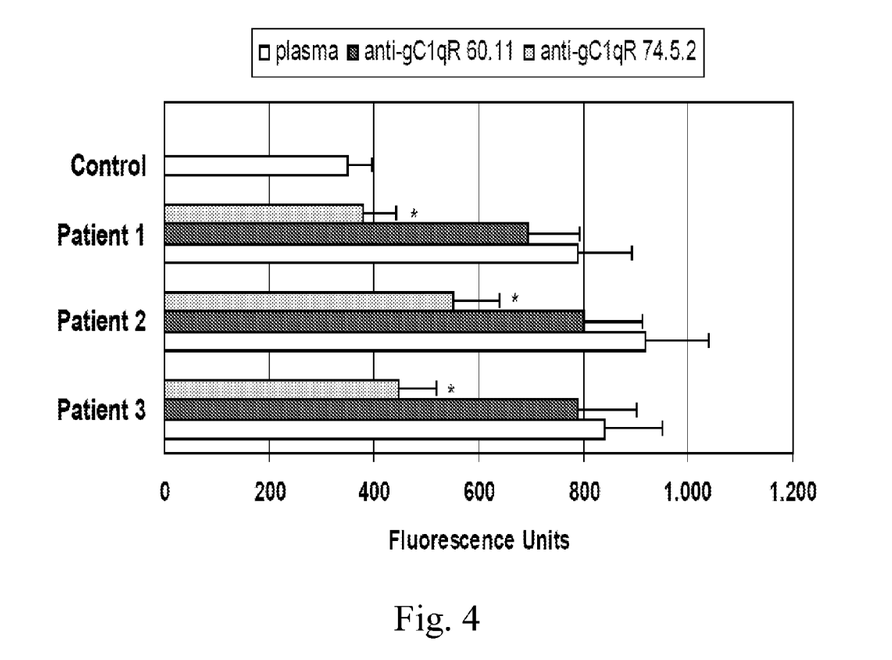
FIG. 4. A monolayer of HUVECs was incubated with two different mAbs anti-gC1q-R (20 µg/ml) for 10 minutes prior to incubation with plasma samples obtained from AE patients (during the attack phase) for additional 30 minutes (*p<0.01 vs plasma). See, Bossi et al., 2009, J. Allergy Clin. Immunol. 124:1303-1310.

The role played by the gC1q-R receptor in the enhancement of increased permeability induced by the attack phase plasma of AE patients was investigated. (Bossi, et al. 2009, J. Allergy Clin. Immunol. 124:1303-1310). The results depicted in FIG. 4 show that the permeabilizing effect of plasma collected from 3 different patients (patients with hereditary angioedema A, B and patient with acquired angioedema C) was prevented by the presence of mAb 74.5.2 (20 µg/ml) that inhibits the binding of HK to gC1q-R, but not by the monoclonal antibody 60.11 (20 µg/ml) that recognizes another epitope not involved in the interaction with the HK.

In the transwell model of vascular permeability, the amount of FITC-BSA passed through the EC monolayers in the lower chamber at different time points was measured by a fluorometer. Plasma from C1-INH deficient patients collected during an angioedema attack (henceforth referred to as attack plasma) and during remission were tested and analyzed (Tedesco, Cicardi, Ghebrehiwet). As shown in FIG. 4, negligible levels of FITC-BSA were detected when ECs were incubated for 30 minutes with medium or medium supplemented with plasma from controls or from patients in remission (*p<0.01 vs control). Conversely, a two to three-fold increase in the FITC-BSA level was induced with plasma of patients.

Example 5

Blocking the Interaction of HK with gC1q-R

Figure 5:
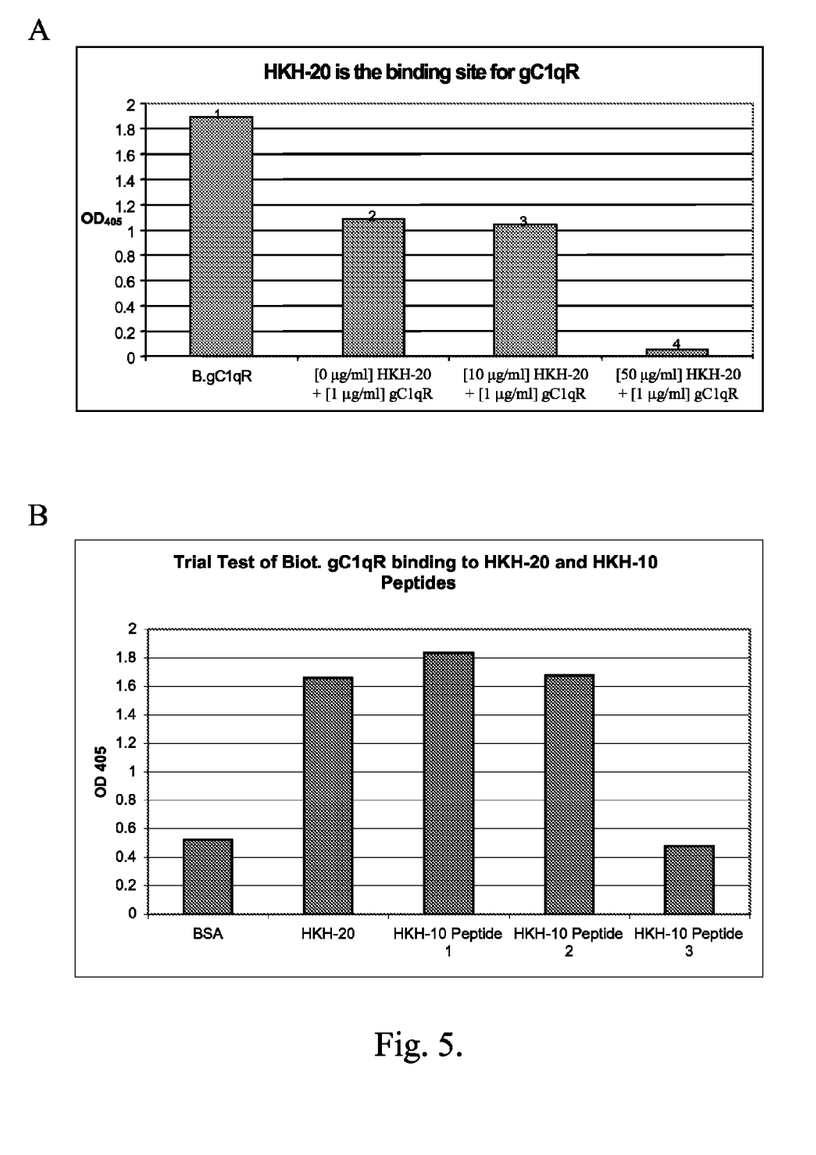

As discussed earlier, gC1q-R binds HK through a site on domain 5 that is located on the light chain of HK. A 20 amino acid-long peptide corresponding to 479-498 (HKHGHGH-GKHKNKGKKNGKH; SEQ ID NO:11) has been shown to be the site for interaction with domain 5 and this peptide can be used to inhibit the interaction of HK with intact endothelial cells. Highly purified recombinant gC1q-R was used to demonstrate that the HK site for gC1q-R is contained within the residues corresponding to this peptide. This experiment was performed by competitive binding studies in which ELISA plate wells coated with 100 µg/ml HK peptide were incubated with biotinylated gC1q-R (1 µg/ml) in the presence or absence of increasing concentrations of peptide as a solution phase competitor. As shown in FIG. 5A, while gC1q-R bound strongly to the HK peptide, its binding was totally inhibited in the presence of 50 µg/ml HKH20. Furthermore, experiments performed using 10-residue overlapping peptides generated from HKH20 showed that the gC1q-R binding site on HKH20 involves the histidine-rich domain corresponding to residues 479-488 (SEQ ID NO:13). (FIG. 5B)

Example 6

Identification of Novel C1q Sites on gC1q-R

Figure 6:
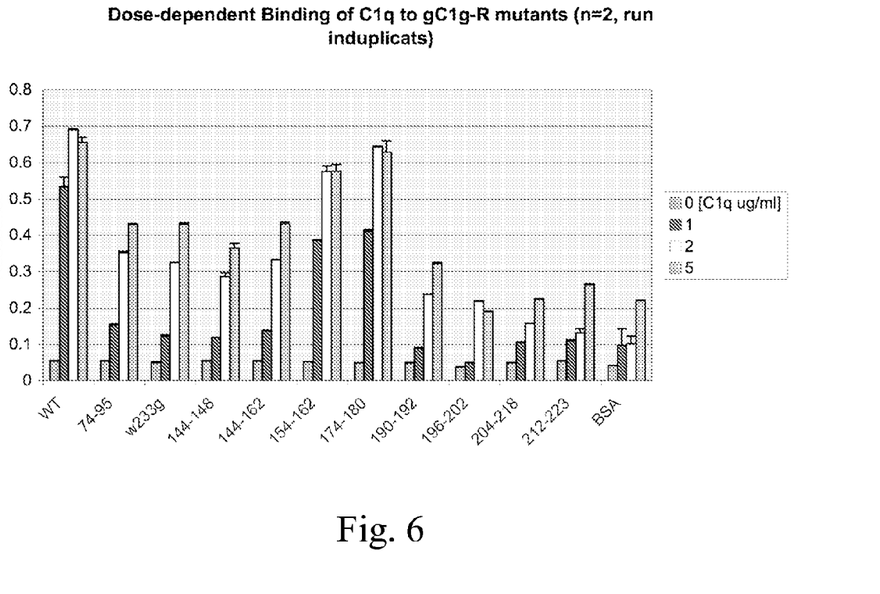
FIG. 6. Shows the identification of novel C1q sites on gC1q-R using deletion gC1q-R mutants.

By peptide mapping and antibody inhibition studies we had identified previously C1q binding sites. Deletion mutants were used to verify previous sites or identify novel sites. Deletion mutants are gC1q-R proteins lacking a specific domain predicted from its 3D structure to contain a binding site for a ligand—in this case C1q or HK. The deleted domain in turn may be a single amino acid, or 20 amino acids-long contiguous segment. Using this logic, we generated several recombinant gC1q-R proteins by deletion of domains of very high negative charge. The capabilities of these mutants to support C1q binding were then examined in a dose-dependent manner by comparing to the binding of the full-length gC1q-R. Analyses of the data reveal the presence of at least three additional binding sites for C1q contained within residues 190-192, 196-202 and 204-218 (FIG. 6) in addition to the primary target (amino acid residues 76-93 within residues 74-95 (SEQ ID NO:1).

Example 7

Identification of HK Sites on gC1q-R

Figure 7:
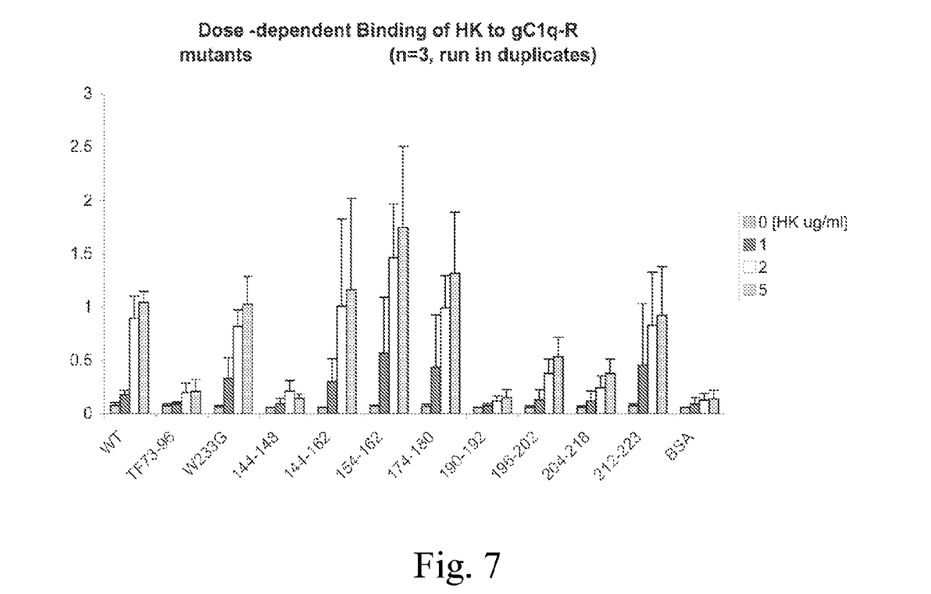
FIG. 7. Shows the identification of novel HK sites on gC1q-R using deletion gC1q-R mutants.

Using the deletion mutants described in Example 6, we performed similar studies using HK as a ligand. As shown in FIG. 7, we confirmed that the original domain (amino acids 204-218) described as a potential HK site indeed contains an HK site as evidenced by the lack of HK binding to a mutant lacking these residues. In addition however, there appear to be several potential sites in TF73-96, W233G (a tryptophan at position 233 substituted by glycine), 144-148, and 190-192.

The experiments described in the following Example are intended to represent possible embodiments of the present invention. It is understood that the materials and amounts do not limit the scope of the invention.

Example 8

Intravital Microscopy in Rats and Hamsters

All of the examples provided in the previous sections demonstrate that the interaction between HK and gC1q-R and to a less extent, the interaction between C1q and gC1q-R is involved in the generation of vasoactive peptides such as bradykinin. Although in vitro models of vascular permeability are useful for screening reagents that inhibit vascular leakage, another method to test the therapeutic potential of peptides or antibodies is in animal models using a method called intravital microscopy. The permeabilizing activity of plasma samples obtained from the AE patients or any agent that induces AE is monitored by the intravital microscopy model in either rats and hamsters. These in vivo animal models are used to evaluate the therapeutic efficacy of agents that inhibit the interaction of gC1q-R and HK. Plasma samples collected from at least 10 patients affected by the different types of angioedema are tested in the in vivo models in duplicates as described below.

The permeabilizing activity of the plasma samples obtained from the AE patients is monitored by the intravital microscopy model in rats and hamsters. These in vivo animal models are used to evaluate the therapeutic efficacy of agents that inhibit the interaction of gC1q-R and HK. Plasma samples collected from at least 4 patients affected by the different types of angioedema are tested in the in vivo models in duplicates.

Rats: Initial experiments are performed on approximately 50 male Wistar Kyoto rats weighing between 250 and 270 g, anesthetized with sodium thiobarbitol as described in detail in a previous publication (Bossi et al. 2004. J. Immunol. 173: 6921-6927). A catheter inserted into the left carotid artery, and a Statham P23AC pressure transducer (Gould, Cleveland, Ohio) connected to a physiograph are used to monitor the mean arterial pressure and the heart rate as described (Bossi et al. 2004. J. Immunol. 173:6921-6927). Then, FITC-BSA diluted in sterile saline, is infused into the femoral vein and a portion of the ileal mesentery is gently draped over a transparent Plexiglas pedestal placed on an adjustable stage of an upright microscope. Attack or remission phase or control plasma is topically applied to the exposed mesentery, and the amount of FITC-BSA leaking out of the mesenteric venules into the perivenular interstitium is evaluated. The images of the distribution of FITC-BSA are recorded by a camera connected to a computer and analyzed off-line using dedicated imaging software. To examine the inhibitory activity of anti-gC1q-R mAbs, various concentrations of serum-free and endotoxin-free mAbs generated by in vitro ascitis (IVA) are applied.

Using this method, mAb 74.5.2 can be shown to block vascular permeability by 50-80%. Similarly, blocking of vascular permeability by other agents that inhibit the interaction of gC1q-R with HK can be evaluated by this method.

Hamsters: Changes are characterized in hamsters using AE plasma or BK. As angioedema occurs in the oral mucosa, the hamster cheek pouch is used as a model. Golden hamsters are anesthetized (sodium pentobarbital, 70 mg/kg, i.p.), tracheostomized and an indwelling right jugular catheter is placed. Intravital observations are made using the superfused cheek pouch, prepared as previously documented (Fox et al. Microvasc. Res. 64: 414-424; Frame and Mabanta. 2007. Microcirculation, 14(7): 739-754). The tissue is superfused with a bicarbonate buffered physiological salt solution (in mmol/l: 131.9 NaCl, 4.7 KCl, 2.0 $CaCl_2$, 1.2 $MgSO_4$, and 18 $NaHCO_3$, pH 7.4±0.05 at 37° C.) which is equilibrated with gas containing 0% $O_2$, 5% $CO_2$, and the balance $N_2$. The tissue is visualized using a modified Nikon E400 upright fixed stage microscope, with objective magnification of 60×. Arteriole tone is verified by dilation to brief topical $10^{-4}$M adenosine, and constriction to 10% oxygen added to the suffusate gas. There is a 60 min stabilization period preceding data collection.

Systemic hematocrit is sampled prior to and after the experiments, to verify hydration state of the animal. To make measurements of permeability, fluorescent dye (FITC conjugated to dextran at 4 kD, 70 kD and 150 kD) is injected as a 50 µl bolus via the jugular catheter, while observations are made of 20 µm post-capillary venules. Using an intensified charge coupled device (ICCD, Solamere Technology Group) at fixed gain, the venule and associated interstitial area are videotaped and analyzed off-line to determine the grey scale value. The specific regions of interest are the centerline of the venule itself, which will be used to calculate the total load of dye delivered to the vessel, and the interstitial area 50 µm perpendicular to the wall of the venule, which will be monitored over time for appearance of the dye (i.e., permeability). The dye concentration is calibrated to the intravascular light signal, as before (Rivers et al. 2001. Anesthesiology, 94: 489-495; Frame et al. 2002. Am. J. of Physiol. Heart and Circulation. 282: H2377-H2385), and to known interstitial levels in 6 hamsters. The dye concentration delivered to the venule, and the rate of appearance of the dye concentration within the tissue is used as a measure of permeability.

Resistance changes in the arterioles and venules are directly measured, and red blood cell velocity is determined, using a well-established protocol with fluorescently labeled red blood cells (Fox et al. Microvasc. Res. 64: 414-424; Frame and Mabanta. 2007. Microcirculation, 14(7): 739-754). These cells are obtained from age- and weight-matched donor hamsters, labeled with rhodamine isothiocyanate (XRITC), and injected via the jugular catheter during the 60 min stabilization period. The flow is videotaped and analyzed off-line using automated particle motion analysis software (ProAnalyst, ExCitx). The cell velocity is obtained as the distance traveled over 1/60th s on sequential video fields. Harmonic mean velocity, V, and diameter, D, are used to calculate the fluid shear rate, $\gamma$, where $\gamma=8$ V/D. Measurements of baseline permeability, flow and diameter are made prior to exposure to test agents. Permeability measurements are made 10 minutes apart following administration of each MW dextran bolus; repeated measures with this bolus injection technique are possible even with significant permeability changes because the tissue bath flow rate of 5 ml/min washes away residual interstitial dye and remaining intravascular dye is filtered by the kidney within minutes. The test agents are added to the suffusate, and measures are repeated at 30, 60, 90, 180 and 270 minutes after exposure. For each test agent, one concentration is tested per animal. Eight animals are used per dose of test agent.

Of the antibodies so far tested, mAb 74.5.2 appears to block vascular permeability both in rats and Syrian hamsters. The peptides that have the potential to do the same are gC1q-R peptides (SEQ ID:5; SEQ ID:7; SEQ ID:8) and HK peptides (SEQ ID:11, SEQ ID:12, SEQ ID NO:13, SEQ ID NO:14).

TABLE 1

Peptide Sequences

| SEQ ID NO: | Gene | Amino acid range | Amino acid sequence |
|---|---|---|---|
| 1 | gC1q-R | 76-93 | TDGDKAFVDFLSDEIKEE |
| 2 | gC1q-R | 144-162 | DGEEEPSQGQKVEEQEPEL |
| 3 | gC1q-R | 144-148 | DGEEE |
| 4 | gC1q-R | 174-180 | KNDGKKEL |
| 5 | gC1q-R | 190-202 | EDEVGQEDEAESD |
| 6 | gC1q-R | 196-202 | EDEAESD |
| 7 | gC1q-R | 190-192 | EDE |
| 8 | gC1q-R | 204-218 | FSIREVSFQSTGESE |
| 9 | gC1q-R | 215-218 | GESE |
| 10 | gC1q-R | 212-223 | QSTGESEWKDTN |
| 11 | HK | 479-498 | HKHGHGHGKHKNKGKKNGKH |

TABLE 1-continued

Peptide Sequences

| SEQ ID NO: | Gene | Amino acid range | Amino acid sequence |
|---|---|---|---|
| 12 | HK | 487-498 | KHKNKGKKNGKH |
| 13 | HK | 479-488 | HKHGHGHGKH |
| 14 | HK | 484-493 | GHGKHKNKGK |
| 15 | HK | 489-498 | KNKGKKNGKH |
| 16 | HK | 487-491 | KHKNK |

TABLE 2

Monoclonal antibodies

| mAb Name | Inhibition Site | Amino acid Range | Target Amino Acid Sequence | SEQ ID NO: |
|---|---|---|---|---|
| 60.11 | C1q | 76-93 | TDGDKAFVDFLSDEIKEE | 1 |
| 74.5.2 | HK | 204-218 | FSIREVSFQSTGESE | 8 |
| 48. | HK | 190-202 | EDEVGQEDEAESD | 5 |
| 83.1 | HK | 190-202 | EDEVGQEDEAESD | 5 |

I claim:

1. A method of treating angioedema in a patient in need thereof comprising administering to the patient a therapeutically effective amount of an agent that is capable of inhibiting the interaction of HK with gC1q-R, wherein the agent binds to the HK binding site of gC1q-R or wherein the agent binds to a gC1q-R binding site of HK.

2. The method of claim 1, wherein the agent comprises an antibody or polypeptide.

3. The method of claim 2, wherein the agent is an antibody that binds to a HK-binding site of gC1q-R.

4. The method of claim 2, wherein the antibody binds to a gC1q-R binding site of HK.

5. The method of claim 2, wherein the agent is a polypeptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, and SEQ ID NO:16.

6. The method of claim 1, wherein the patient is taking an ACE inhibitor.

* * * * *